US008876086B2

(12) United States Patent
Burke et al.

(10) Patent No.: US 8,876,086 B2
(45) Date of Patent: Nov. 4, 2014

(54) FRAGRANCE EMITTER

(75) Inventors: Eric Kent Burke, Ammon, ID (US);
Deborah M. Merrill, Ammon, ID (US)

(73) Assignee: Cierra Ashley, LLC, Idaho Falls, ID (US)

( * ) Notice: Subject to any disclaimer, the term of this patent is extended or adjusted under 35 U.S.C. 154(b) by 345 days.

(21) Appl. No.: 13/398,819

(22) Filed: Feb. 16, 2012

(65) Prior Publication Data

US 2012/0205462 A1   Aug. 16, 2012

Related U.S. Application Data

(60) Provisional application No. 61/443,499, filed on Feb. 16, 2011.

(51) Int. Cl.
*B01F 3/04* (2006.01)
*A61L 9/12* (2006.01)

(52) U.S. Cl.
CPC ............ *A61L 9/122* (2013.01); *A61L 2209/134* (2013.01); *Y10S 261/88* (2013.01)
USPC ........ 261/30; 261/99; 261/107; 261/DIG. 88; 422/124

(58) Field of Classification Search
CPC ........ B01F 3/04; B01F 3/04085; A62B 11/00

USPC ................... 261/30, 99, 107, DIG. 88; 239/8; 422/124

See application file for complete search history.

(56) References Cited

U.S. PATENT DOCUMENTS 5,547,721 A * 8/1996 Kuo .............................. 428/34.1
6,106,786 A * 8/2000 Akahoshi ...................... 422/124

* cited by examiner

*Primary Examiner* — Robert A Hopkins
(74) *Attorney, Agent, or Firm* — Kunzler Law Group, PC

(57) ABSTRACT

An apparatus for emitting a fragrance includes an enclosure that has at least one inlet and at least one outlet. The at least one outlet has a cross-sectional area smaller than a cross-sectional area of the at least one inlet. The enclosure further includes a Venturi-type nozzle that defines the at least one outlet. The apparatus also includes a fragrance source positioned within the enclosure and an air mover positioned within the enclosure. The air mover is operable to draw fresh air into the enclosure through the at least one inlet and drive the drawn fresh air across the fragrance source to transfer fragrance material from the fragrance source to the fresh air to form an air-fragrance mixture. The Venturi-type nozzle of the enclosure accelerates the air-fragrance mixture through the at least one outlet.

19 Claims, 5 Drawing Sheets

FRAGRANCE EMITTER

CROSS-REFERENCE TO RELATED APPLICATION

This application claims the benefit of U.S. Provisional Patent Application No. 61/443,499, filed Feb. 16, 2011, which is incorporated herein by reference.

FIELD

This application is related generally to air fresheners, and more particularly to a forced convection device for emitting a fragrance.

BACKGROUND

For years, devices for emitting fragrances into the air have been used to adjust the smell of a space. Some devices are configured to passively emit fragrances into the air, while others are designed to actively or forcefully emit fragrances into the air. Passive fragrance emitting devices rely only on stagnant or naturally-induced airflow to diffuse a fragrance into the air via unforced convection and/or radiation. In contrast, active fragrance emitting devices rely on artificially-induced airflow to diffuse a fragrance into the air primarily via forced convection. Many passive and/or active fragrance emitters known in the art require heat, a flame, wax, smoke, or some other catalyst in order to activate or effectively distribute fragrances, which results in certain distinct disadvantages and shortcomings.

Although artificially-induced airflow type devices offer advantages over passive airflow type devices, artificially-induced devices still suffer from several shortcomings. For example, known fragrance emitting devices that use a fan or other air moving device to induce an air flow often fail to provide an adequate degree of control over the strength of the fragrance being omitted. In other words, once activated, these fragrance emitting devices emit fragrance at a fixed volumetric flow rate and until the fragrance source is empty. Attempting to provide some control over the rate at which fragrance is emitted, some devices employ one or more adjustable vanes to adjust the size of the openings through which the fragrance is deployed into the air. However, the adjustable vanes merely affect the fluid flow dynamics after the fragrance is diffused into the air, such that the rate at which the fragrance is diffused remains the same.

Certain artificially-induced fragrance emitting devices also fail to adequately spread or diffuse the fragrance over a sufficiently large space. The flow coming out of such devices is often too concentrated to adequately diffuse throughout a given space.

SUMMARY

The subject matter of the present application has been developed in response to the present state of the art, and in particular, in response to the problems and needs in the art that have not yet been fully solved by currently available fragrance-emitting devices. Accordingly, the subject matter of the present application has been developed to provide various embodiments of a device and system for emitting fragrances that overcomes at least some of the above or other shortcomings of the prior art.

Generally, according to at least some embodiments, described herein is a system configured to emit a fragrance into an open space in a controllable, efficient, and widely dispersed manner. The system forcefully draws air into an aerodynamically-shaped enclosure, directs the air upward and around a fragrance-saturated wick, and accelerates the air upward through an opening into the open space. The number of wicks is easily adjustable to control the concentration of fragrance emitted into the open space. Further, the acceleration of the air through the opening promotes a wide distribution and large coverage area of the air and fragrance in the open space. These and other advantages of the system are accomplished without heat, flame, wax, or smoke.

According to one embodiment, an apparatus for emitting a fragrance includes an enclosure that has at least one inlet and at least one outlet. The at least one outlet has a cross-sectional area smaller than a cross-sectional area of the at least one inlet. The enclosure further includes a Venturi-type nozzle that defines the at least one outlet. The apparatus also includes a fragrance source positioned within the enclosure between the at least one inlet and at least one outlet. Additionally, the apparatus includes an air mover positioned within the enclosure between the at least one inlet and the fragrance source. The air mover is operable to draw fresh air into the enclosure through the at least one inlet and drive the drawn fresh air across the fragrance source to transfer fragrance material from the fragrance source to the fresh air to form an air-fragrance mixture. The Venturi-type nozzle of the enclosure accelerates the air-fragrance mixture through the at least one outlet.

In some implementations of the apparatus, the air drawn through the at least one inlet flows upwardly through and out of the enclosure. The at least one inlet can be positioned below the at least one outlet, the fragrance source can be positioned below the at least one inlet, and the air mover can be positioned below the fragrance source and above at least one inlet. The air mover may force the fresh air upwardly toward the fragrance source and the air-fragrance mixture exits upwardly through the at least one outlet. The enclosure can include a base surface configured to rest on an object and support the enclosure in a vertical orientation relative to the object.

According to yet some implementations of the apparatus, the fragrance source includes an open container for containing a liquid fragrance. The fragrance source can further include at least one wick that is positionable within the open container. A portion of the at least one wick may extends out of the open container through an opening of the open container. The fragrance source can include a plurality of wicks positionable within the open container. Further, the open container can include an open top where the open top faces away from the air mover.

In certain implementations of the apparatus, the enclosure includes a base and a cover. The cover is removably coupleable to the base. Further, the base and cover define respective portions of an internal cavity of the enclosure. The internal cavity can be defined about a central axis of the enclosure, the at least one inlet can be formed in the base and face a direction substantially perpendicular to the central axis, and the at least one outlet can be formed in the cover and face a direction generally parallel to the central axis.

According to some implementations of the apparatus, a portion of the enclosure between the at least one outlet and the fragrance source includes a converging sidewall that converges in a direction extending from the fragrance source to the at least one outlet. The direction extending from the fragrance source to the at least one outlet is a first direction. The air mover can further drive the drawn fresh air in the first direction. Also, a section of the converging sidewall is positioned adjacent an open end of the fragrance source to redirect at least a portion of the fresh air driven in the first direction in a second direction substantially perpendicular to the first direction across the fragrance source. The at least one outlet can be defined as a portion of the Venturi-type nozzle with a minimum cross-sectional area. Further, the Venturi-type nozzle can include an expansion portion downstream of the at least one outlet. The expansion portion includes a diverging sidewall that diverges in the direction extending from the fragrance source to the at least one outlet.

In certain implementations of the apparatus, the cross-sectional area of the at least one outlet (which, in some implementations, is the combined cross-sectional area of a plurality of outlets) is between about 15% and about 50% smaller than the cross-sectional area of the at least one inlet. In one particular implementation, the cross-sectional area of the at least one outlet is between about 20% and about 30% smaller than the cross-sectional area of the at least one inlet. The at least one inlet can include a plurality of inlets, and the cross-sectional area of the at least one outlet is smaller than a combined cross-sectional area of the plurality of inlets. The apparatus can emit the fragrance without use of a heat source, a flame source, wax, and smoke. In certain implementations, the enclosure includes a substantially cylindrically-shaped bottom section and a substantially blunt conically-shaped top section.

According to some implementations, the apparatus further includes a stand that is removably positionable within the enclosure. The stand includes a first support surface and a second support surface spaced apart from the first support surface. The stand is configured to position the first support surface in a spaced-apart manner relative to a bottom of the enclosure. Moreover, the first support surface supports the air mover and the second support surface supports the fragrance source.

In another embodiment, an apparatus for emitting a fragrance includes a base defining a first interior space and including a plurality of inlets. The apparatus further includes a cover that is removably coupled to the base. The cover defines a second interior space and includes an outlet where a size of the outlet is smaller than a combined size of the plurality of inlets. The apparatus includes a stand removably positioned within the first and second interior spaces. Additionally, the apparatus includes a container with an opening in a top portion of the container. The opening is configured to receive at least one wick and allow the at least one wick to extend therethrough. The container is further configured to retain a liquid fragrance and is supported on the stand and positioned between the plurality of inlets and the outlet. The apparatus also includes a fan supported on the stand in a spaced-apart manner relative to the container. The fan is positioned between the container and the plurality of inlets.

According to one embodiment, a method for emitting a fragrance includes drawing fresh air into an enclosure, directing the fresh air across a fragrance material within the enclosure, transmitting the fragrance material to the fresh air as its directed across the fragrance material to create an air-fragrance mixture, accelerating the air-fragrance mixture through a Venturi-type nozzle, and directing the accelerated air-fragrance mixture out of the enclosure.

Reference throughout this specification to features, advantages, or similar language does not imply that all of the features and advantages that may be realized with the subject matter of the present disclosure should be or are in any single embodiment or implementation of the subject matter. Rather, language referring to the features and advantages is understood to mean that a specific feature, advantage, or characteristic described in connection with an embodiment is included in at least one embodiment of the subject matter of the present disclosure. Discussion of the features and advantages, and similar language, throughout this specification may, but do not necessarily, refer to the same embodiment or implementation.

The described features, structures, advantages, and/or characteristics of the subject matter of the present disclosure may be combined in any suitable manner in one or more embodiments and/or implementations. In the following description, numerous specific details are provided to impart a thorough understanding of embodiments of the subject matter of the present disclosure. One skilled in the relevant art will recognize that the subject matter of the present disclosure may be practiced without one or more of the specific features, details, components, materials, and/or methods of a particular embodiment or implementation. In other instances, additional features and advantages may be recognized in certain embodiments and/or implementations that may not be present in all embodiments or implementations. Further, in some instances, well-known structures, materials, or operations are not shown or described in detail to avoid obscuring aspects of the subject matter of the present disclosure. The features and advantages of the subject matter of the present disclosure will become more fully apparent from the following description and appended claims, or may be learned by the practice of the subject matter as set forth hereinafter.

BRIEF DESCRIPTION OF THE DRAWINGS

In order that the advantages of the subject matter may be more readily understood, a more particular description of the subject matter briefly described above will be rendered by reference to specific embodiments that are illustrated in the appended drawings. Understanding that these drawings depict only typical embodiments of the subject matter and are not therefore to be considered to be limiting of its scope, the subject matter will be described and explained with additional specificity and detail through the use of the drawings, in which.

DETAILED DESCRIPTION

Reference throughout this specification to "one embodiment," "an embodiment," or similar language means that a particular feature, structure, or characteristic described in connection with the embodiment is included in at least one embodiment of the subject matter of the present disclosure. Appearances of the phrases "in one embodiment," "in an embodiment," and similar language throughout this specification may, but do not necessarily, all refer to the same embodiment. Similarly, the use of the term "implementation" means an implementation having a particular feature, structure, or characteristic described in connection with one or more embodiments of the subject matter of the present disclosure, however, absent an express correlation to indicate otherwise, an implementation may be associated with one or more embodiments.

Figure 1:
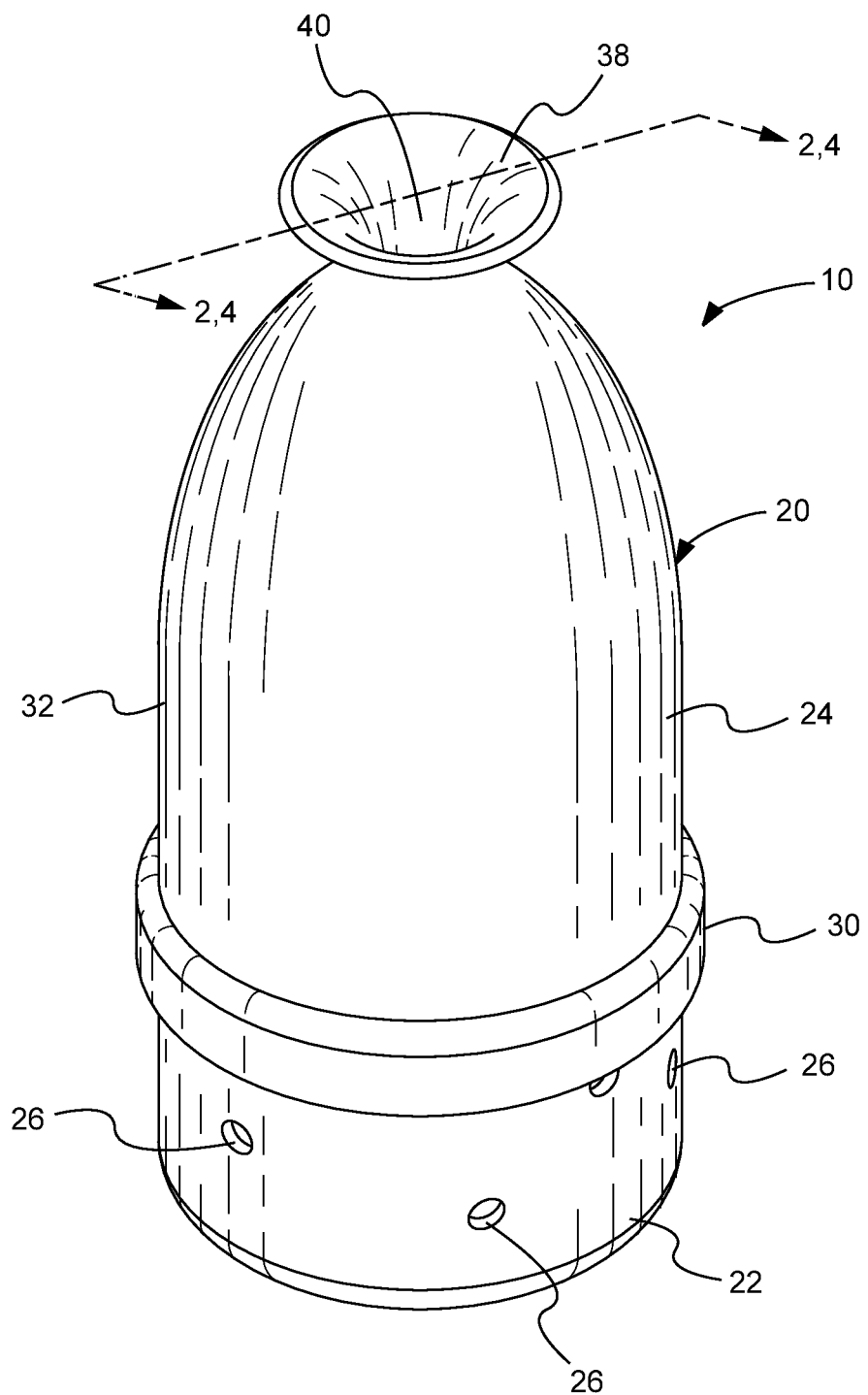
FIG. 1 is a perspective view of a fragrance emitter system according to one embodiment.

As shown in FIG. 1, a fragrance-emitting system 10 includes an aerodynamically-shaped enclosure 20 substantially enclosing an air mover and fragrance source as will be described in more detailed below. The enclosure 20 includes a base 22 removably coupled to a cover 24 via a coupling arrangement 30. The base 22 represents a bottom portion of the enclosure 20 and the cover 24 represents a middle and top portion of the enclosure. In the illustrated embodiment, both the base 22 and cover 24 are formed with a relatively thin-walled construction. For example, the base 22 and cover 24 each include a sidewall 23, 21 defining an interior hollow cavity 46, 44 of the base and cover, respectively. The base 22 includes at least one, and preferably a plurality of, air intake apertures 26 formed in the sidewall 23 of the base. Further, the base 22 can include a substantially flat bottom surface configured to provide stability to the enclosure 20 when supported on a flat object, such as a table, desk, floor, or the like.

The cover 24 includes a lower section 32, upper section 34, neck section 36, and outlet or expansion section 38. The lower section 32 can be defined by a substantially axially straight sidewall 21. In other words, the lower section 32 can have a constant cross-sectional area perpendicular to a central axis 90 of the enclosure 20 along a length of the central axis. The upper section 34 is defined by a substantially axially curved sidewall 21 that converges in an axially upward or inlet-to-outlet direction. In general terms, in some implementations, the combined lower section 32 and upper section 34 of the enclosure 20 is bullet shaped. The neck section 36 defines an opening 40 having a cross-sectional area smaller than the base 22, lower section 32 of the cover 24, upper section 34 of the cover, and outlet section 28 of the cover. The opening 40 is defined as the portion of the neck section 36 with a minimum cross-sectional area, and thus functions as the outlet of the enclosure. In certain implementations, the sidewall 21 of the cover 24 transitions smoothly and contiguously between the lower, upper, neck, and outlet sections 32, 34, 36, 38. In such implementations, the cover 24 may be formed of a monolithic one-piece construction. However, in other implementations, the sections of the cover 24 may be formed separately and assembled together to form the cover 24. Generally, in certain embodiments, the base 22 is a hollow, substantially cylindrically-shaped element, and the cover 24 is a hollow, substantially blunt conically-shaped (e.g., bottle-shaped) element.

Figure 2:
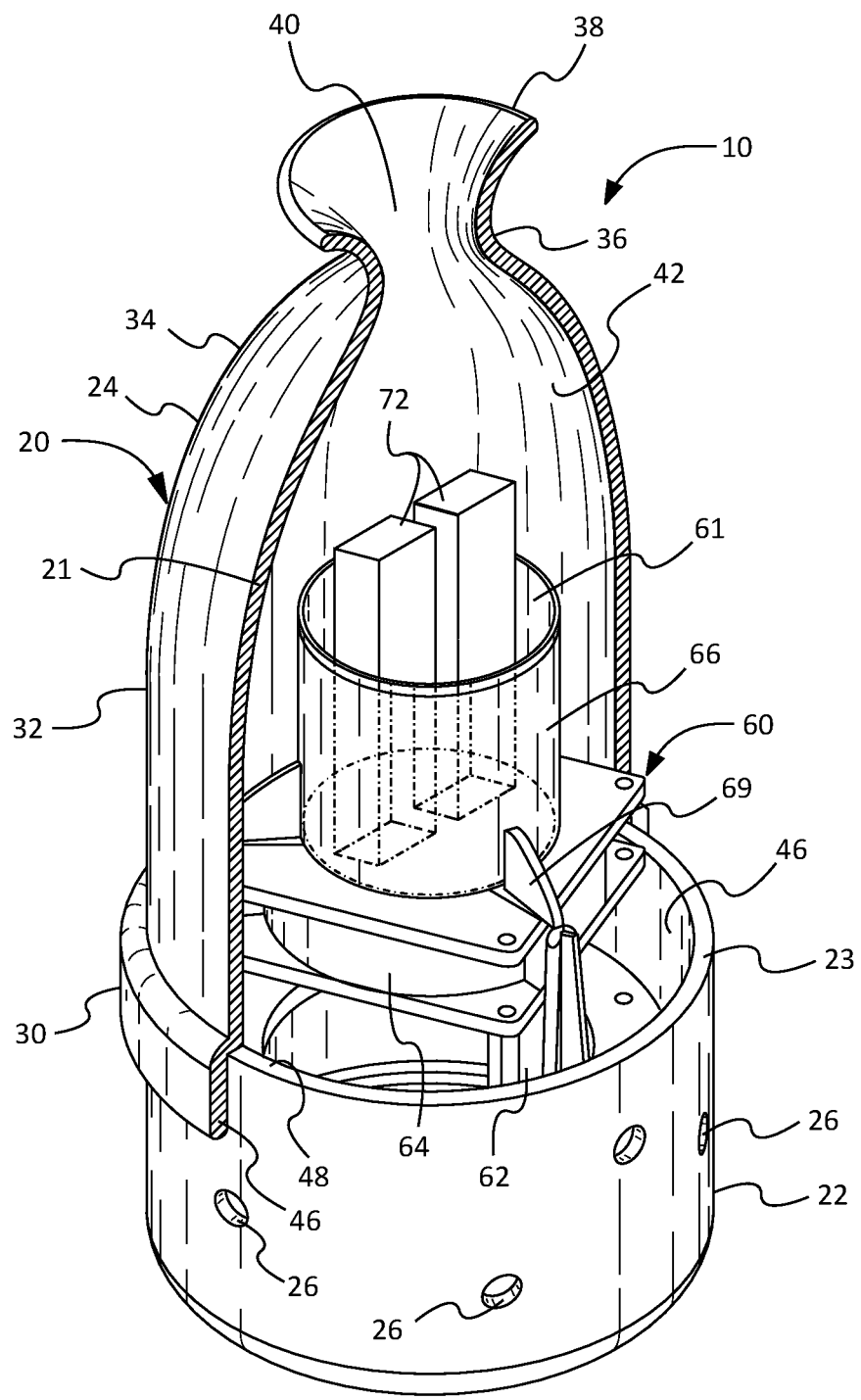
FIG. 2 is a partial cross-sectional perspective view of the fragrance emitter system of FIG. 1 showing a fragrance generator positioned within an enclosure of the system.

The base 22 couples to and supports the cover 24 via the coupling arrangement 30. As shown in FIG. 2, the coupling arrangement 30 includes a raised ridge or lip 30 of the cover 24 matingly receiving an upper rim 48 of the base 22. In alternative embodiments, the components of the coupling arrangement 30 can be reversed such that the raised ridge or lip 46 is formed in the base 22 and receives the rim 48, which forms part of the cover 24. In yet other embodiments, any of various other coupling arrangements may be employed to couple the cover 24 to the base 22.

The base 22 and cover 24 can be made from any of various materials that can be formed (e.g., shaped and/or molded) into the shapes of the base and cover. For example, in one embodiment, at least one of the base 22 and cover 24 are made from a ceramic material. In other embodiments, at least one of the base 22 and cover 24 is made from polymeric material, such as a hardened plastic. Alternatively, in some embodiments, at least one of the base 22 and cover 24 is made from a metal.

Figure 3:
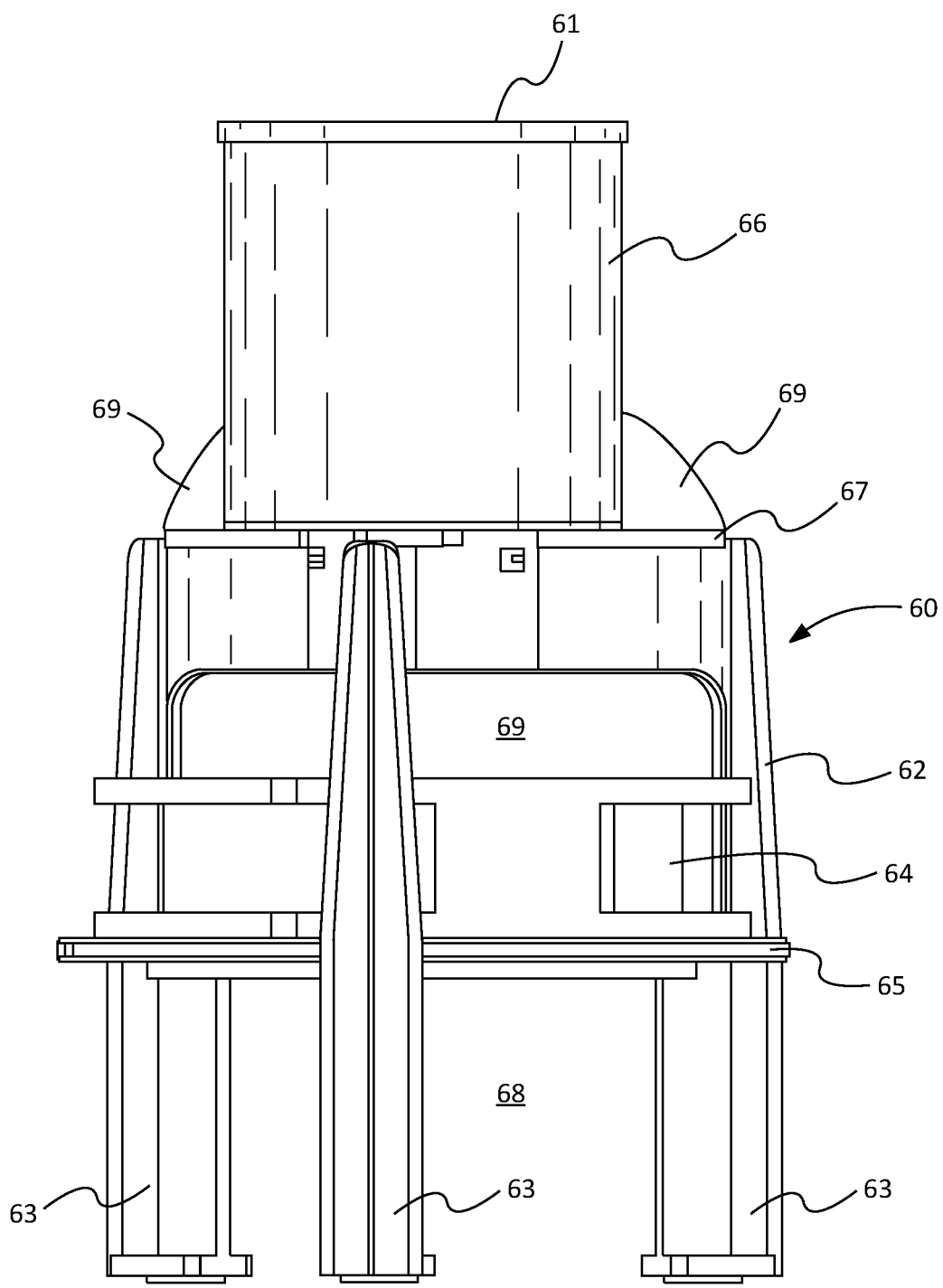
FIG. 3 is a side view of a stand of the fragrance generator shown in FIG. 2.

Also shown in FIG. 2, the fragrance-emitting system 10 includes a fragrance generator 60 positioned within the enclosure 20. The fragrance generator 60 includes a stand 62 having legs 63 extending between a container support surface 67 and an air mover support surface 65 (see FIG. 3). The surfaces 65 and 67, or objects defining the surfaces, are secured to the legs 63 in a spaced-apart configuration. The surfaces 65, 67 can be defined as a top surface of a supporting object, such as a plate, ribbing, arms, beams, annular rings, etc. Accordingly, the surfaces 65, 67 need not define a solid, homogenous, and planar surface, but can comprise a group of smaller narrow surfaces defined about openings that allow air to flow past the surfaces relatively unobstructively. The legs 63 terminate at a distal end below the air mover support surface 65. Accordingly, when positioned within the enclosure 60, the legs 63 act as a spacer to define an air receiving space 68 below the air mover support surface 65 and within the interior cavity of the base 22. The length of the legs 63 extending below the air mover support surface 65 is sufficient to allow air to access the space 68 via the plurality of air intake apertures 26 formed in the base 22. The surfaces 65 and 67 of the stand 62 also are spaced-apart to define an air flow space 69 between (e.g., directly vertically between) the container support surface 67 and an outlet of an air mover 64 supported on the air mover support surface 65 as shown in FIG. 3. Accordingly, as will be described below in more detail, the air mover is positioned substantially directly vertically beneath the container.

Although the stand 62 in the illustrated embodiments includes three legs 63, in other embodiments, the stand can have fewer or more than three legs. For example, in one implementation, the stand 62 can include a single leg in the form of cylindrically-shaped stand-off. The stand-off could have apertures for facilitating the flow of air from outside the enclosure 20 through the apertures 26 in the base and into the air receiving space 68. Additionally, although the illustrated embodiment of the stand 62 has legs 63 that each extends uninterruptedly from the container support surface 67 to below the air mover support surface 65, in some embodiments, the legs 63 may include separate subsections with a first set of subsections extending between the surfaces 65, 67, and the second set of subsections extending from the surface 65 to a distal location below the surface 65. The stand 62 can be made from any of various materials, such as plastics, metal, and the like. In some implementations, the stand 62 is formed with a one-piece monolithic construction, such as from a molding process.

The fragrance generator 60 also includes the air mover 64 and a fragrance container 66. The air mover 64 is supported on the support surface 65, and can be retained on or secured to the support surface 65 via any of various techniques, such fastening techniques, bonding techniques, adhesive techniques, hook-and-loop techniques, and the like. Generally, the air mover 64 can be any device operable to draw air into the space 68 below the air mover and force air upwardly into the space above the air mover. In one embodiment, the air mover is a fan. The fan can be electrically powered via an AC power supply (e.g., a wall outlet) or a DC power supply (e.g., batteries). Accordingly, the system 20 may include a plug-in power adapter that electrically couples, and converts if necessary, power between a wall outlet and the fan. Alternatively, the system 20 can be a stand-alone or tether-less system without a wall mounted power adapter, such as with a battery-powered fan. In certain implementations, the speed of the fan is adjustable by controlling the power supplied to the fan. For example, the fan 64 can include a switch or control panel that not only is user-engageable to turn the fan on and off, but also to adjust the speed of the fan as desired. As will be described in more detail below, controlling the speed of the fan consequently and proportionately controls the amount of fragrance emitted from the system 10. Although the illustrated embodiment of the air mover 64 may be a fan, other air movers, such as pumps, actuators, compressors, and the like.

The fragrance container 66 can be any of variously sized and shaped containers capable of containing a liquid or non-liquid concentrated fragrance. The container 66 includes a closed bottom and sides, and an at least partially open top. The container 66 is supported on the support surface 67 such that the closed bottom of the container directly faces the output of the air mover 64, and the open top of the container 66 faces a direction substantially opposite the output of the air mover. Although the container 66 of the illustrated embodiments includes a completely open top, in other embodiments, the open top can be partially closed. For example, in one embodiment, the container 66 may include a removable cap with one or more apertures sized to allow at least one wick to extend therethrough. The container 66 is removably secured to the surface 67 such that the container, when empty of its contents (e.g., concentrated fragrance) or when a change of fragrance is desired, can be easily removed from the stand 62 and refilled and/or replaced. To maintain the position of the container 66 on the surface 67, the stand 62 can include upwardly protruding tabs 69 spaced about the surface 67. In some implementations, the tabs 69 are an upward extension of the arms 63.

Forming part of the fragrance generator 60, one or more wicks 72 are positioned within the container 66 in contact with the fragrance 70 (e.g., fragrance material) stored in the container. In one embodiment, the fragrance is a liquid and each wick 72 includes a length of fibrous or pulpy material, such as paper, cardboard, wood, or the like. The fibrous material absorbs the liquid fragrance until the entire wick is saturated. The length of the wicks 72 are such that while in fluid contact with the stored fragrance, an upper portion of the wick is positionable above the level of the fragrance. Preferably, the wick is long enough that the upper portion is also positionable above the container 66 (e.g., extends upward through the opening 61 in the container 66. In one implementation, as shown, each wick 72 is long enough that it can be bent in a U-shape, with two ends positioned within the fragrance and a bent portion (e.g., upper portion) positioned above the opening 61 of the container 66. Although two wicks 72 are shown in the illustrated embodiments, one or more than two wicks (e.g., 3-8 wicks) can be used.

The fragrance generator 60, including the stand 62, can have any of various sizes and shapes depending on the size and shape of the internal cavities 44, 46 of the cover and base, respectively, which collectively define an internal cavity of the enclosure. In the illustrated embodiment, the internal cavities of the enclosure 20 have a generally circular-shaped cross-section along a plane perpendicular to the central axis 90 of the enclosure. Accordingly, in such an embodiment, the fragrance generator 60 can have a generally circular-shaped cross-section of a size small enough to fit within the confines of the enclosure 20. Alternatively, the fragrance generator 60 can have any cross-sectional shape, configuration, or size, as long as it fits within the confines of the enclosure. In the illustrated embodiment, the support surface 65 has a generally circular-shaped outer periphery corresponding with the generally circular-shaped cross-section of the base 22. In some implementations, the support surface 65 matingly engages the interior surface 43 of the base 22 to at least partially support, maintain, and/or stabilize the fragrance generator 60 in an upright position. Additionally, the distal end of the arms 63 may include feet that rest on a bottom interior surface 43 of the base 22 to provide additional support and stabilization for maintaining the fragrance generator 60 in an upright position.

Assembly of the fragrance-emitting system 10 is accomplished, in one embodiment, by coupling the air mover 65 to the surface 65 of the stand 62 and positioning the stand in the base 22. The container 66 is at least partially filled with a desired fragrance and one or more wicks 67 is placed in contact with the fragrance to be at least partially saturated with the fragrance. The container 66 with the fragrance and wicks is positioned on the support surface 67. Then, the cover 24 is placed over the fragrance generator 60 and coupled with the base 22 to substantially enclose the generator within the enclosure 20. For operation, the air mover 64 is actuated (e.g., turned on) to draw fresh air into the enclosure 20, drive the air across the wicks to diffuse fragrance into the fresh air, and accelerate the air/fragrance mixture through the restriction neck 36 and into the environment.

Figure 4:
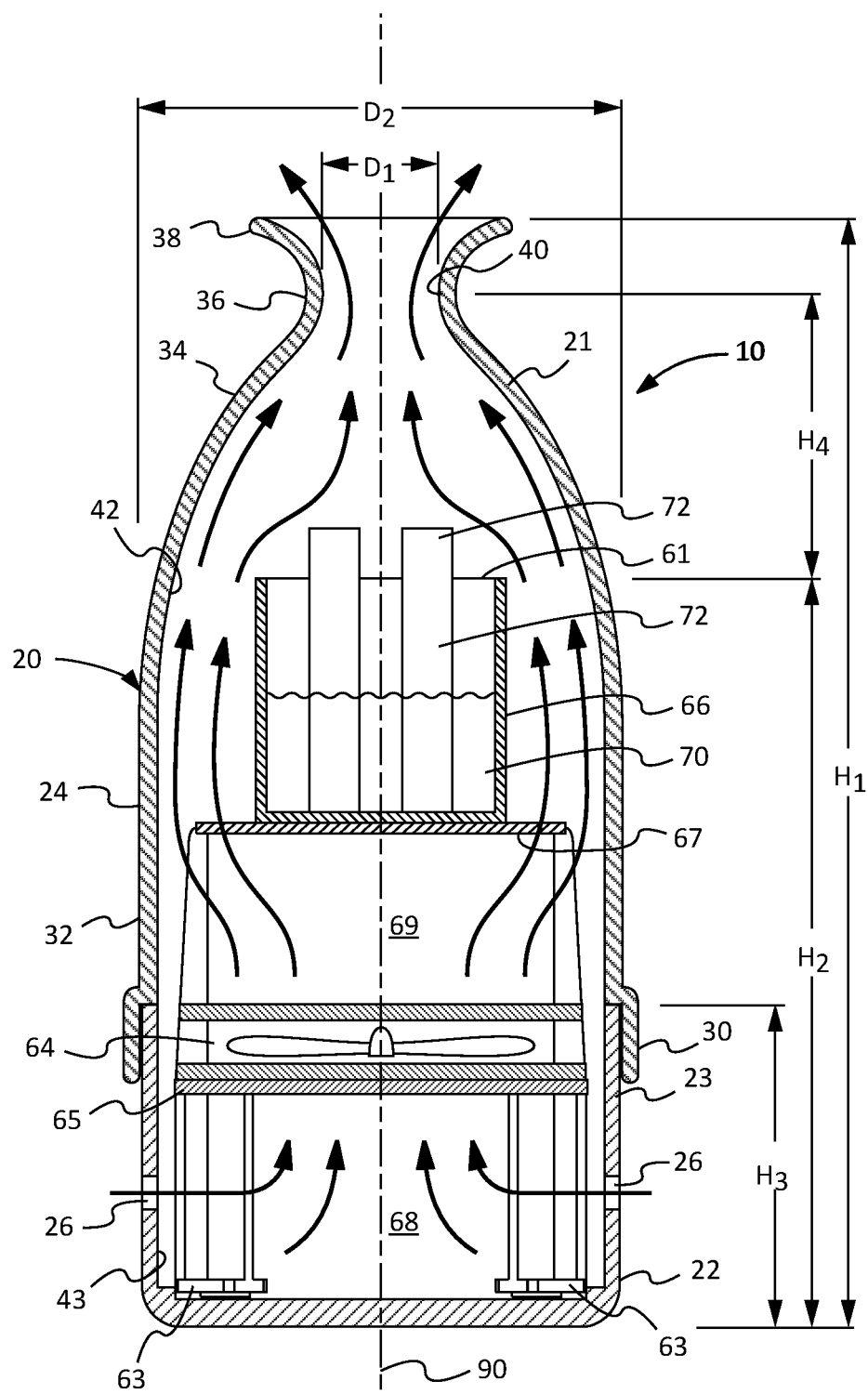
FIG. 4 is cross-sectional side view of a fragrance emitter system according to one embodiment.

A representation of the air and fragrance flow pattern through the system 10 is shown in FIG. 4 with the flow patterns represented generally by a plurality of directional arrows. Activation of the air mover 64 (e.g., switching a fan to the ON position) draws fresh air from the environment (e.g., air external to the system 10) into the interior of the enclosure 20 through the plurality of apertures 26 formed in the base 22. After entering the internal space 68 defined by the base 22, the air is forced substantially upward due to the pull of the fan 64, through the fan, and into the internal space 69 between the fan and the support surface 67. From the internal space 69, the fresh air continues to be driven upwardly by the fan 64. The fresh air in the internal space 69 driven upwardly toward the container 66 is redirected around the container due to the boundary layer formed on the surface of the container. Accordingly all the fresh air entering the enclosure 20 is driven upwardly around the container 66.

As discussed above, the sidewall 21 of the top section 34 of the cover 24 converges in an upward direction. Accordingly, the internal surface 42 of the converging top section 34 acts as a funnel to draw the fresh air radially inwardly toward the central axis 90 of the enclosure 20. As the air is drawn radially inwardly, a substantial portion of the fresh air passes over the exposed portions of the wicks 72 above the container opening 61 (and to a lesser degree the exposed portions of the wicks below the opening 61). Because the exposed portions are saturated with fragrance, the fragrance is transferred via convection to the air passing over the exposed portions of the wicks 72 to form an air/fragrance mixture. The fragrance transferred from the wicks 72 is replaced by additional fragrance due to the absorbing action of the material forming the wicks. The container opening 61 defined at the top of the container 66 faces away from the outlet of the air mover 64 such that the air driven through the fan does not directly contact the fragrance in the container, which would happen if the opening and fragrance were directly facing the outflow of the fan.

Following the transfer of fragrance to the air, the air/fragrance mixture is forced upwardly and slightly radially inwardly due to the concavity or converging nature of the top section 34 of the cover 24. Because the cross-sectional area of the top section 34 decreases in an upward direction, a Venturi-type nozzle is created, and the air/fragrance mixture is accelerated and the pressure of the mixture is decreased due to a Venturi effect induced by the converging sidewall 21. The velocity of the mixture continuously accelerates and the pressure of the mixture continuously decreases until the mixture reaches the outlet 40 defined by the restriction neck 36. The outlet 40 is defined as the portion of the neck 36 with the smallest diameter. In this manner, the enclosure, and more particularly, the restriction neck includes a Venturi nozzle to accelerate the air-fragrance mixture out of the enclosure.

Further, due to the Venturi effect induced by the converging nature of the upward section 34, the higher pressure air/fragrance mixture built-up behind the lower pressure mixture forces to continuously accelerate and drive the mixture upwardly through the outlet 40. Although the illustrated embodiments include a single outlet 40 and Venturi nozzle, in other embodiments, the enclosure can include multiple outlets 40 and Venturi nozzles.

After passing through the outlet 40, the diverging sidewalls 21 of the outlet section 38 facilitate rapid expansion and wide distribution of the accelerated air/fragrance mixture. The restriction neck 36 of the enclosure 20 introduces a gradual transition from converging to diverging sidewalls. The rate of convergence of the upper section 34 of the cover 24 may be the same as or different than the rate of divergence of the outlet section 38 of the cover. In one embodiment, the rate of convergence of the upper section 34 of the cover 24 is less than the rate of divergence of the outlet section 38 of the cover. For curved surfaces, the rate of convergence and divergence can be defined by the radius of curvature of the surface. For example, a minimum radius of curvature of the interior surface 42 of the upper section 34 may be greater than a minimum radius of curvature of the interior surface 42 of the outlet section 38. For example, in one implementation, the radius of curvature of the upper section 34 transitions from a radius of curvature of about 7.4 inches upwardly to a radius of curvature of about 5.8 inches, and the radius of curvature of the upper section 34 is about 0.68 inches (e.g., a ratio of about 10.9 and about 8.5, respectively). Generally, the greater the rate of divergence or minimum radius of curvature of the outlet section 38, the wider (e.g., larger) the horizontal distribution of the air/fragrance mixture from the enclosure 20 and the shallower (e.g., smaller) the vertical distribution of the mixture. In contrast, the lesser the rate of divergence or minimum radius of curvature of the outlet section 38, the narrower (e.g., smaller) the horizontal distribution of the air/fragrance mixture from the enclosure 20 and the taller (e.g., larger) the vertical distribution of the mixture.

Additionally, the distribution of the mixture expelled out of the enclosure is dependent on the size (e.g., diameter $D_1$) of the neck section 36 and outlet 40. Generally, the smaller the outlet 40, the faster the velocity of the mixture through the outlet 40, and the greater the distribution, both horizontally and vertically. In contrast, the larger the outlet 40, the slower the velocity of the mixture through the outlet 40, and the lesser the distribution, both horizontally and vertically. However, the size of the outlet 40 of the enclosure 20 desirably falls within a range between variable lower and upper limits. The upper and lower limits are dependent upon several factors, including the combined cross-sectional area of the inlet apertures 26 and the air moving capacity or rating of the air mover 64. For example, if the ratio of the cross-sectional area of the inlet apertures 26 to the cross-sectional area of the outlet 40 is too high, or if the air moving capacity of the air mover 64 is too high relative to the size of the outlet 40, a high amount of backpressure may buildup within the enclosure, which may affect the air flow patterns through the enclosure and disrupt the operation of the system 10. In contrast, if the ratio of cross-sectional areas of the inlet apertures 26 and outlet 40 is too low, or if the air moving capacity of the air mover 64 is too low relative to the size of the outlet 40, the necessary Venturi effect induced by the restriction neck may be negated, resulting in a low acceleration and poor distribution of fragrance out of the system 10.

Accordingly, based on the application (e.g., room size, room height, etc.), the rate of divergence of the outlet section 38, capacity of the air mover 64, and/or size of the outlet 40 can be selected to achieve a desired distribution of fragrance out of the system 10 or a desired performance or efficiency of the system. In some implementations, the ratio of cross-sectional area of the inlet apertures 26 to that of the outlet 40 is between about 1.15 and about 1.50 (e.g., the area of the outlet 40 is between about 15% and about 50% smaller than the combined area of the inlet apertures). Accordingly, the amount of air flowing out of the outlet 40 is between about 15% and about 50% less than the amount of air entering the apertures 26. In yet certain implementations, the area of the outlet 40 is between about 20% and about 30% smaller than the combined area of the inlet apertures, such that the amount of air flowing out of the outlet 40 is between about 20% and about 30% less than the amount of air entering the apertures 26. In some implementations, the air mover 64 is a fan driven by a motor that is configured to generate an airflow between about 5 cfm (cubic feet per minute) and about 15 cfm. In certain implementations, the DC power rating of the fan's motor can be between about 1.5V and about 12V.

Additionally, other dimensions of the system 10 can be configured to achieve a desired distribution of fragrance out of the system or desired performance or efficiency of the system. For example, the overall height $H_1$ and diameter of the enclosure $D_2$ can be selected to achieve a desired air flow within the enclosure. In one implementation, the overall height $H_1$ is about 12.5 inches and the diameter $D_2$ is about 5 inches (e.g., a ratio of about 2.5). The overall height H1 can also be dependent on the rating or capacity of the air mover, and vice versa. For example, the higher the overall height H1, the higher the rating or capacity of the air mover needs to be to keep the backpressure within the enclosure significant enough in a larger volume to accelerate the air/fragrance mixture out of the enclosure.

Additionally, the distances or heights $H_2$, $H_3$, $H_4$ between the components of the system 10 can affect the performance of the system 10. For example, the $H_2$ is the distance between the bottom of the enclosure 20 and the open top 61 of the container 66. In some implementations, the height $H_2$ is selected based on the overall height $H_1$ of the enclosure 20 and where along the enclosure the top section 34 begins to converge, as well as radius of curvature. The height $H_2$ can be such that the top portion 34 begins to curve at a height that is less than the height $H_2$. In some implementations, the lower the radius of curvature of the top section 34 (e.g., the more curved the top section 34), the lower the height $H_2$. The height $H_2$ is also dependent upon the height of the container 66, or more specifically, the height of the sidewalls of the container. Moreover, the height of the container 66 is selected based on the capacity of the air mover. With lower capacity air movers, less air is flowing through the enclosure making it harder for the air to be force into contact with the fragrance within the container. Therefore, for lower capacity air movers, the height of the container 66 should be less to accommodate the lower air flow rate. In contrast, for higher capacity air movers, the height of the container 66 can be higher because the air flow rate is higher and can reach the fragrance within the higher-walled container.

As shown, $H_3$ is the distance between the bottom of the enclosure and the outlet of the air mover 64. In certain implementations, the height $H_3$ should be sufficient to allow enough space for the drawn-in air to flow upward thorough the air mover without creating unnecessary restrictions (e.g., backpressure) within the space 68. Finally, $H_4$ is the distance between the open top 61 of the container and the outlet 40 or the narrowest part of the neck portion 36. In some implementations, the distance $H_3$ is selected based on a desired recirculation and backpressure within the top section 34 of the enclosure.

Figure 5:
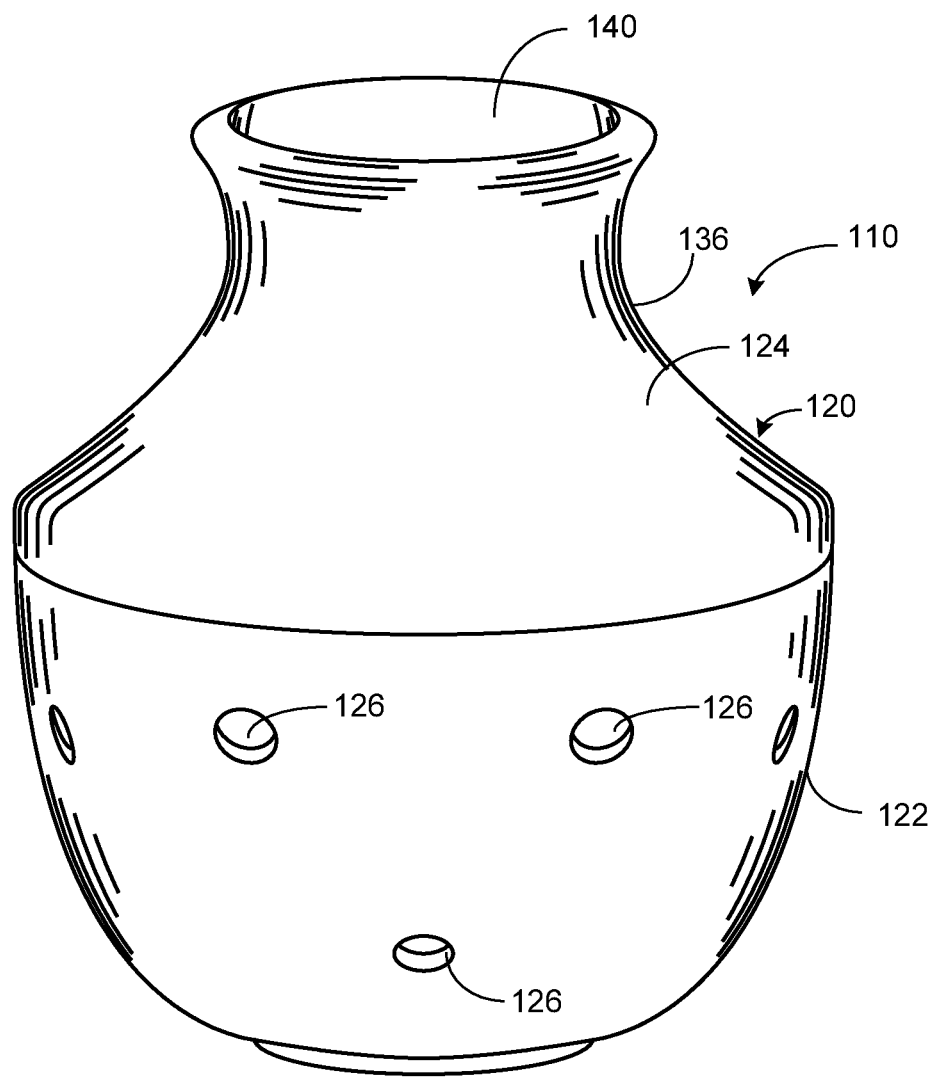
FIG. 5 is a perspective view of a fragrance emitter system according to another embodiment.

The system 10 can have any of various proportions for accommodating enclosures of any of various heights and sizes. For example, referring to FIG. 5, a system 110 includes an enclosure 120 that is substantially shorter than the enclosure 20 of the system 10. Correspondingly, the height and relative spacing of the fragrance generator (not shown) positioned within the enclosure 120 are shorter and smaller, respectively. Further, although the entire enclosure 120 of the system 110 can have a generally circular cross-sectional shape along planes perpendicular to a central axis of the enclosure 120, as with enclosure 20, in the illustrated embodiments, the base 122 of the enclosure, as well as a portion of the cover 124, have a substantially quadrangular cross-sectional shape along the same planes. The enclosure 120 gradually upwardly transitions from a substantially quadrangular cross-sectional shape to a substantially circular cross-sectional shape at the neck section 136 of the enclosure. Additionally, in some implementations, the enclosure 120 gradually downwardly transitions from a substantially quadrangular cross-sectional shape to a substantially circular cross-sectional shape at a bottom surface of the base 122 of the enclosure. Although a portion of the enclosure 120 has a substantially quadrangular-shaped cross-section, in other embodiments, the enclosure can have any of various other cross-sectional shapes, such as circular, triangular, ovular, polygonal, and the like. Generally, the system 110 includes features analogous to the features of the system 10, with like numbers referring to like elements. For example, the base 122 includes a plurality of inlets 126 and the cover 124 includes an accelerations nozzle defining an outlet 140 of the enclosure 120.

Although the above-illustrated embodiments are shown in a vertical or upright implementation, in other implementations, the system 10 can be used in a sideways or upside down configuration. For example, the stand 60 can be reconfigured to support the container 66 in a sideways orientation (i.e., rotated 90-degrees relative to the orientation shown in the Figures) to retain the fragrance in the container. However, the other features could remain substantially the same.

In the above description, certain terms may be used such as "up," "down," "upper," "lower," "horizontal," "vertical," "left," "right," and the like. These terms are used, where applicable, to provide some clarity of description when dealing with relative relationships. But, these terms are not intended to imply absolute relationships, positions, and/or orientations. For example, with respect to an object, an "upper" surface can become a "lower" surface simply by turning the object over. Nevertheless, it is still the same object.

The subject matter of the present disclosure may be embodied in other specific forms without departing from its spirit or essential characteristics. The described embodiments are to be considered in all respects only as illustrative and not restrictive. The scope of the subject matter of the present disclosure is, therefore, indicated by the appended claims rather than by the foregoing description. All changes which come within the meaning and range of equivalency of the claims are to be embraced within their scope.

What is claimed is:

1. An apparatus for emitting a fragrance, comprising:
    an enclosure comprising at least one inlet and at least one outlet, the at least one outlet having a cross-sectional area smaller than a cross-sectional area of the at least one inlet, wherein the enclosure further comprises a Venturi-type nozzle defining the at least one outlet, and wherein the enclosure comprises a base and a cover, the cover being removably coupleable to the base, and wherein the base and cover define respective portions of an internal cavity of the enclosure;
    a fragrance source positioned within the enclosure between the at least one inlet and at least one outlet; and
    an air mover positioned within the enclosure between the at least one inlet and the fragrance source, the air mover being operable to draw fresh air into the enclosure through the at least one inlet and drive the drawn fresh air across the fragrance source to transfer fragrance material from the fragrance source to the fresh air to form an air-fragrance mixture;
    wherein the Venturi-type nozzle of the enclosure accelerates the air-fragrance mixture through the at least one outlet.

2. The apparatus of claim 1, wherein the air drawn through the at least one inlet flows upwardly through and out of the enclosure.

3. The apparatus of claim 2, wherein the at least one inlet is positioned below the at least one outlet, the fragrance source is positioned below the at least one inlet, and the air mover is positioned below the fragrance source and above at least one inlet, wherein the air mover forces the fresh air upwardly toward the fragrance source and the air-fragrance mixture exits upwardly through the at least one outlet.

4. The apparatus of claim 2, wherein the enclosure comprises a base surface configured to rest on an object and support the enclosure in a vertical orientation relative to the object.

5. The apparatus of claim 1, wherein the fragrance source comprises an open container for containing a liquid fragrance.

6. The apparatus of claim 5, wherein the fragrance source further comprises at least one wick positionable within the open container, wherein a portion of the at least one wick extends out of the open container through an opening of the open container.

7. The apparatus of claim 6, wherein the fragrance source comprises a plurality of wicks positionable within the open container.

8. The apparatus of claim 5, wherein the open container comprises an open top, and wherein the open top faces away from the air mover.

9. The apparatus of claim 1, wherein the internal cavity is defined about a central axis of the enclosure, the at least one inlet being formed in the base and facing a direction substantially perpendicular to the central axis, and the at least one outlet being formed in the cover and facing a direction generally parallel to the central axis.

10. The apparatus of claim 1, wherein a portion of the enclosure between the at least one outlet and the fragrance source comprises a converging sidewall that converges in a direction extending from the fragrance source to the at least one outlet.

11. The apparatus of claim 10, wherein the direction extending from the fragrance source to the at least one outlet is a first direction, wherein the air mover further drives the drawn fresh air in the first direction, and wherein a section of the converging sidewall is positioned adjacent an open end of the fragrance source to redirect at least a portion of the fresh air driven in the first direction in a second direction substantially perpendicular to the first direction across the fragrance source.

12. The apparatus of claim 10, wherein the at least one outlet is defined as a portion of the Venturi-type nozzle with a minimum cross-sectional area, and wherein the Venturi-type nozzle comprises an expansion portion downstream of the at least one outlet, the expansion portion comprising a diverging sidewall that diverges in the direction extending from the fragrance source to the at least one outlet.

13. The apparatus of claim 1, wherein the cross-sectional area of the at least one outlet is between about 15% and about 50% smaller than the cross-sectional area of the at least one inlet.

14. The apparatus of claim 1, wherein the at least one inlet comprises a plurality of inlets, and wherein the cross-sectional area of the at least one outlet is smaller than a combined cross-sectional area of the plurality of inlets.

15. The apparatus of claim 1, wherein the apparatus emits the fragrance without use of a heat source, a flame source, wax, and smoke.

16. The apparatus of claim 1, wherein the enclosure comprises a substantially cylindrically-shaped bottom section and a substantially blunt conically-shaped top section.

17. The apparatus of claim 1, further comprising a stand removably positionable within the enclosure, the stand comprising a first support surface and a second support surface spaced apart from the first support surface, the stand configured to position the first support surface in a spaced-apart manner relative to a bottom of the enclosure, wherein the first support surface supports the air mover and the second support surface supports the fragrance source.

18. An apparatus for emitting a fragrance, comprising:
- a base defining a first interior space, the base comprising a plurality of inlets;
- a cover removably coupled to the base, the cover defining a second interior space and comprising an outlet, a size of the outlet being smaller than a combined size of the plurality of inlets, wherein the cover comprises a Venturi-type nozzle defining the outlet;
- a stand removably positioned within the first and second interior spaces;
- a container comprising an opening in a top portion of the container, the opening configured to receive at least one wick and allow the at least one wick to extend therethrough, the container further configured to retain a liquid fragrance, wherein the container is supported on the stand and positioned between the plurality of inlets and the outlet; and
- a fan supported on the stand in a spaced-apart manner relative to the container, the fan being positioned between the container and the plurality of inlets, the fan being operable to draw fresh air into the first and second interior spaces through the plurality of inlets and drive the drawn fresh air across the at least one wick to transfer the liquid fragrance from the at least one wick to the fresh air to form an air-fragrance mixture;

wherein the Venturi-type nozzle of the cover accelerates the air-fragrance mixture through the outlet.

19. A method for emitting a fragrance, comprising:
- drawing fresh air into an enclosure, the enclosure comprising at least one inlet and at least one outlet, the at least one outlet having a cross-sectional area smaller than a cross-sectional area of the at least one inlet, wherein the enclosure further comprises a Venturi-type nozzle defining the at least one outlet, and wherein the enclosure comprises a base and a cover, the cover being removably coupleable to the base, and wherein the base and cover define respective portions of an internal cavity of the enclosure;
- directing the fresh air across a fragrance material within the enclosure using an air mover positioned within the enclosure between the at least one inlet and the fragrance material;
- transmitting the fragrance material to the fresh air as its directed across the fragrance material to create an air-fragrance mixture;
- accelerating the air-fragrance mixture through the Venturi-type nozzle; and
- directing the accelerated air-fragrance mixture out of the enclosure.

* * * * *